United States Patent
Jain et al.

(10) Patent No.: US 10,482,634 B2
(45) Date of Patent: Nov. 19, 2019

(54) SYSTEMS AND METHODS FOR IMAGING WITH ANISOTROPIC VOXELS

(71) Applicant: General Electric Company, Schenedtady, NY (US)

(72) Inventors: Nitin Jain, Bangalore (IN); Sangtae Ahn, Guilderland, NY (US); Steven Ross, Pewaukee, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 176 days.

(21) Appl. No.: 15/792,363

(22) Filed: Oct. 24, 2017

(65) Prior Publication Data
US 2019/0122399 A1    Apr. 25, 2019

(51) Int. Cl.
G06T 11/00    (2006.01)
G06T 3/40    (2006.01)
A61B 6/03    (2006.01)

(52) U.S. Cl.
CPC ............ *G06T 11/008* (2013.01); *A61B 6/037* (2013.01); *G06T 3/4007* (2013.01); *G06T 11/006* (2013.01); *G06T 11/005* (2013.01); *G06T 2207/10104* (2013.01)

(58) Field of Classification Search
None
See application file for complete search history.

(56) References Cited

U.S. PATENT DOCUMENTS

| | | | |
|---|---|---|---|
| 6,754,298 B2 | 6/2004 | Fessler | |
| 7,583,780 B2* | 9/2009 | Hsieh | A61B 6/032 378/4 |
| 7,856,129 B2* | 12/2010 | Panin | G06T 11/005 382/128 |
| 7,885,371 B2 | 2/2011 | Thibault et al. | |
| 7,983,465 B2 | 7/2011 | Leroux et al. | |

(Continued)

OTHER PUBLICATIONS

Fessler, J. A., & Rogers, W. L. (Oct. 1994). Uniform quadratic penalties cause nonuniform spatial resolution. In Proceedings of 1994 IEEE Nuclear Science Symposium-NSS'94 (vol. 4, pp. 1915-1919). IEEE. (Year: 1994).*

(Continued)

*Primary Examiner* — Michelle M Entezari
(74) *Attorney, Agent, or Firm* — Dean D. Small; The Small Patent Law Group, LLC

(57) ABSTRACT

An imaging system is provided that includes at least one detector configured to acquire imaging information, a processing unit, and a display unit. The processing unit is operably coupled to the at least one detector, and is configured to reconstruct an image using the imaging information. The image is organized into voxels having non-uniform dimensions. The processing unit is configured to perform a penalized likelihood (PL) image reconstruction using the imaging information. The PL image reconstruction includes a penalty function. Performing the penalty function includes interpolating a voxel size in at least one dimension from an original size to an interpolated size before determining a penalty function, determining the penalty function using the interpolated size to provide an initial penalty, interpolating the initial penalty to the original size to provide a modified penalty, and applying the modified penalty in the PL image reconstruction.

20 Claims, 5 Drawing Sheets

(56) References Cited

U.S. PATENT DOCUMENTS

| | | | | |
|---|---|---|---|---|
| 8,165,385 | B2* | 4/2012 | Reeves | G06T 7/0012 |
| | | | | 382/128 |
| 8,503,750 | B2* | 8/2013 | Benson | A61B 6/5258 |
| | | | | 378/4 |
| 8,655,033 | B2* | 2/2014 | Zeng | G06T 11/006 |
| | | | | 382/128 |
| 9,269,144 | B2* | 2/2016 | Kraus | A61B 3/102 |
| 9,443,330 | B2* | 9/2016 | Heigl | G06T 11/008 |
| 9,595,121 | B2 | 3/2017 | Ahn et al. | |
| 2005/0226375 | A1* | 10/2005 | Eberhard | A61B 6/482 |
| | | | | 378/62 |
| 2006/0002509 | A1* | 1/2006 | Claus | G06T 11/005 |
| | | | | 378/21 |
| 2007/0217666 | A1 | 9/2007 | Gal et al. | |
| 2008/0217540 | A1 | 9/2008 | Panin et al. | |
| 2008/0317198 | A1 | 12/2008 | Thornton | |
| 2009/0164458 | A1 | 6/2009 | Jung et al. | |
| 2009/0175562 | A1 | 7/2009 | Pan et al. | |
| 2010/0014732 | A1 | 1/2010 | Vija et al. | |
| 2010/0054394 | A1 | 3/2010 | Thibault et al. | |
| 2011/0097007 | A1* | 4/2011 | Zeng | G06T 11/006 |
| | | | | 382/260 |
| 2011/0103669 | A1 | 5/2011 | Michel et al. | |
| 2012/0177274 | A1 | 7/2012 | Koehler et al. | |
| 2013/0208963 | A1 | 8/2013 | Leal et al. | |
| 2014/0111508 | A1 | 4/2014 | Bystrov et al. | |
| 2014/0363066 | A1* | 12/2014 | Ntziachristos | G06T 11/006 |
| | | | | 382/131 |
| 2017/0337687 | A1* | 11/2017 | Wang | G06T 7/11 |

OTHER PUBLICATIONS

Qi, J. (2006). Comparison of statistical reconstructions with isotropic and anisotropic resolution in PET. IEEE transactions on nuclear science, 53(1), 147-151. (Year: 2006).*

Stayman, J. Webster, and Jeffrey A. Fessler. "Compensation for nonuniform resolution using penalized-likelihood reconstruction in space-variant imaging systems." IEEE transactions on medical imaging 23.3 (2004): 269-284. (Year: 2004).*

Stayman, J. Webster, and Jeffrey A. Fessler. "Nonnegative definite quadratic penalty design for penalized-likelihood reconstruction." 2001 IEEE Nuclear Science Symposium Conference Record (Cat. No. 01CH37310). vol. 2. IEEE, 2001. (Year: 2001).*

Gang, G. J., Siewerdsen, J. H., & Stayman, J. W. (Mar. 2016). Task-driven tube current modulation and regularization design in computed tomography with penalized-likelihood reconstruction. In Medical Imaging 2016: Physics of Medical Imaging (vol. 9783, p. 978324). (Year: 2016).* fieldtriptoolbox.org (Year: 2015).*

Aguiar et al. Geometrical and Monte Carlo projectors in 3D PET reconstruction, Oct. 2010, Med. Phys. 37 (11). pp. 5691-5702.

Ahn et al., "Analysis of Resolution and Noise Properties of Nonquadratically Regularized Image Reconstruction Methods for PET", Medical Imaging, IEEE Transactions on, pp. 413-424, vol. 27, Issue 3, Mar. 3, 2008.

Fessler et al., "Spatial Resolution Properties of Penalized-Likelihood Image Reconstruction: Space-Invariant Tomographs" Image Processing, IEEE Transactions on, pp. 1346-1358, vol. 5, Issue 9, Sep. 9, 1996.

Ortuno et al., Efficient methodologies for system matrix modelling in iterative image reconstruction for rotating high-resolution, PETPhys. Med. Biol. 55 (2010) pp. 1833-1861.

Qi et al., "Resolution and Noise Properties of MAP Reconstruction for Fully 3-D PET", Medical Imaging, IEEE Transactions on, pp. 493-508, vol. 19, Issue 5, May 5, 2000.

Stayman, "Spatial Resolution in Penalized-Liklihood image reconstruction", A Dissertation Submitted in Partial Fulfillment of the Requirements for the Degree of Electrical Engineering and Computer Science, pp. 1-239, 2003.

Wang et al., "Penalized Likelihood PET Image Reconstruction Using Patch-based Edge-preserving Regularization", Medical Imaging, IEEE Transactions on, pp. 1, vol. PP, Issue 99, Aug. 2, 2012.

Hsu, "An Investigation of Block-Sequential Algorithms in Statistical PET Image Reconstruction" Journal of Medical and Biological Engineering, 24 (2): 77-83, May 4, 2004.

Sah, et al. "Clinical evaluation of a new block sequential regularized expectation maximization (BSREM) reconstruction algorithm in PET/CT studies" jnm.snmjournals, vol. 55.

* cited by examiner

SYSTEMS AND METHODS FOR IMAGING WITH ANISOTROPIC VOXELS

BACKGROUND OF THE INVENTION

The subject matter disclosed herein relates generally to apparatus and methods for diagnostic medical imaging, such as, for example, positron emission tomography (PET) imaging.

PET is a medical imaging technique that provides functional information regarding physiological processes of an object (e.g., human patient) being imaged. Radiopharmaceuticals may be administered to a patient, resulting in emitted positrons, which undergo annihilation with electrons, generating photons that travel in opposite directions. The photons may be detected, with each event stored in an array referred to as a sinogram. The measured sinogram data may be used to reconstruct a three-dimensional distribution corresponding to the radiopharmaceutical as part of an image reconstruction.

The image matrix used in medical imaging such as PET may have anisotropic voxels, or voxels having non-uniform size in at least one dimension with respect to the other dimensions. During an iterative reconstruction, voxels having a longer length in one dimension may result in over-smoothing in that direction and/or step artifacts, for example.

BRIEF DESCRIPTION OF THE INVENTION

In one embodiment, an imaging system is provided that includes at least one detector configured to acquire imaging information, a processing unit, and a display unit. The processing unit is operably coupled to the at least one detector, and is configured to reconstruct an image using the imaging information. The image information is organized into voxels having non-uniform dimensions. The processing unit is configured to perform a penalized likelihood (PL) image reconstruction using the imaging information. The PL image reconstruction includes a penalty function. Performing the penalty function includes interpolating a voxel size in at least one dimension from an original size to an interpolated size before determining a penalty function, determining the penalty function using the interpolated size to provide an initial penalty, interpolating the initial penalty to the original size to provide a modified penalty, and applying the modified penalty in the PL image reconstruction.

In another embodiment, a method is provided that includes acquiring, with at least one detector, imaging information. The method also includes reconstructing an image using the imaging information. The image is organized into voxels having non-uniform dimensions. Reconstructing the image includes performing a penalized likelihood (PL) image reconstruction using the imaging information. The PL image reconstruction includes a penalty function. Performing the penalty function includes interpolating a voxel size in at least one dimension from an original size to an interpolated size before determining a penalty function, determining the penalty function using the interpolated size to provide an initial penalty, interpolating the initial penalty to the original size to provide a modified penalty, and applying the modified penalty in the PL image reconstruction. The method also includes displaying the image generated using the PL image reconstruction.

In another embodiment, a tangible and non-transitory computer-readable medium is provided that has instructions stored thereon. The instructions, when executed by a computer, causing the computer to acquire, with at least one detector, imaging information; reconstruct an image using the imaging information; and display the image generated. The image is organized into voxels having non-uniform dimensions. Reconstructing the image includes performing a penalized likelihood (PL) image reconstruction using the imaging information. The PL image reconstruction comprising a penalty function. Performing the penalty function includes interpolating a voxel size in at least one dimension from an original size to an interpolated size before determining a penalty function; determining the penalty function using the interpolated size to provide an initial penalty; interpolating the initial penalty to the original size to provide a modified penalty; and applying the modified penalty in the PL image reconstruction.

DETAILED DESCRIPTION OF THE INVENTION

Figure 1:
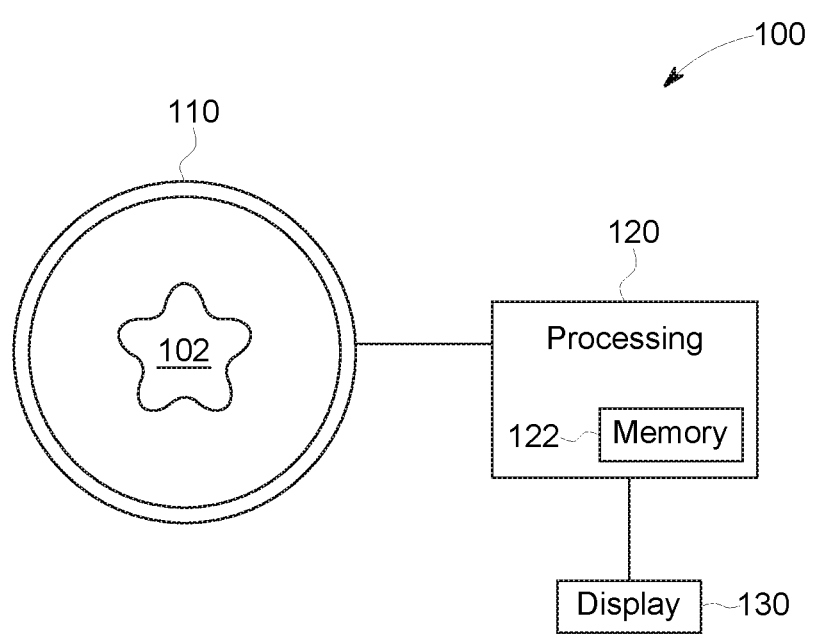
FIG. 1 provides a schematic block view of an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved reconstruction (e.g., for targeted PET imaging such as brain imaging). Various embodiments provide improved reconstruction using penalized likelihood (PL) algorithms. Various embodiments provide more accurate lesion quantitation while providing acceptable visual image quality for PET reconstructions in comparison with, for example, conventional ordered subset expectation maximization (OSEM) algorithms. Generally, PL methods or algorithms use a penalty function that utilizes information from neighboring voxels to control image noise, with the penalty function determined using information from the neighboring 26 voxels. In situations in which large image matrix size and small fields of view are used, for example, voxels may become highly anisotropic as the axial voxel size becomes larger than the transaxial voxel size, resulting in anisotropic penalty computations. Anisotropic penalty computations may result in increased smoothing in the axial direction in certain views (e.g., the coronal and sagittal views for brain imaging) associated with step artifacts. Various embodiments reduce or eliminate adverse effects of anisotropic voxel size and/or anisotropic penalty computations.

PL image reconstruction, which may be referred to as maximum a posteriori (MAP) image reconstruction, includes image reconstruction methods in which a numerical optimization algorithm is used to determine an image that maximizes a PL objective function and thereby provide a reconstructed image. In various embodiments, the PL objective function consists of a likelihood or log-likelihood function, and a regularization function, which may also be referred to as a penalty function or prior distribution.

For example, a PL objective function in various embodiments may be represented as:

$$\Phi(x) = \sum_i y_i \log([Px]_i + r_i) - ([Px]_i + r_i) - \beta R(x)$$

where x denotes a vector representing the activity image, $y_i$ are emission sinogram data, P represents the forward projection operator which includes attenuation, normalization and point spread function resolution modeling, $r_i$ are estimated background contributions including scatter and randoms, R(x) is the regularization or penalty function and $\beta$ is the regularization or penalty parameter.

Further, a penalty function (or relative difference penalty (RDP)) in various embodiments may be represented as:

$$R(x) = \sum_j \sum_{k \in N_j} w_{jk} \sqrt{\beta_j \beta_k} \frac{(x_j - x_k)^2}{x_j + x_k + \gamma|x_j - x_k|}$$

where, $N_j$ is a set of voxels neighboring voxel j, $w_{jk}$ are weights, $\beta_j$, $\beta_k$ are penalty modulation factors and $\gamma$ is a parameter that controls the degree of edge-preservation. In some embodiments a quadratic (or Gaussian) function, a generalized Gaussian function, a Huber penalty, a log-cosh function or a total variation function may be used as the penalty function.

PL image reconstruction may be understood as a process which finds an image that maximizes a PL objective function. In some approaches, when determining a relative difference penalty (RDP) function, weights associated with voxels may be used that correspond to the inverse of distance between neighboring voxels. For example, for a weight $w_{jk}$, where j and k are neighboring voxels, the inverse of the distance between neighboring voxels j and k could be used, where the unit of distance is the voxel. Thus, for equal or isotropic voxel sizes, either 1, 1/sqrt(2), or 1/sqrt(3) may be used for $w_{jk}$, depending on the distance between voxels j and k.

However, for anisotropic voxels, the use of such weights may result in anisotropic smoothing. For example, in a targeted reconstruction scenario for brain imaging where the axial voxel size is sufficiently larger than the transaxial voxel size, increased smoothing in the axial direction (coronal/sagittal planes) may occur. Various embodiments mitigate such smoothing using interpolation during reconstruction.

Figure 2A:
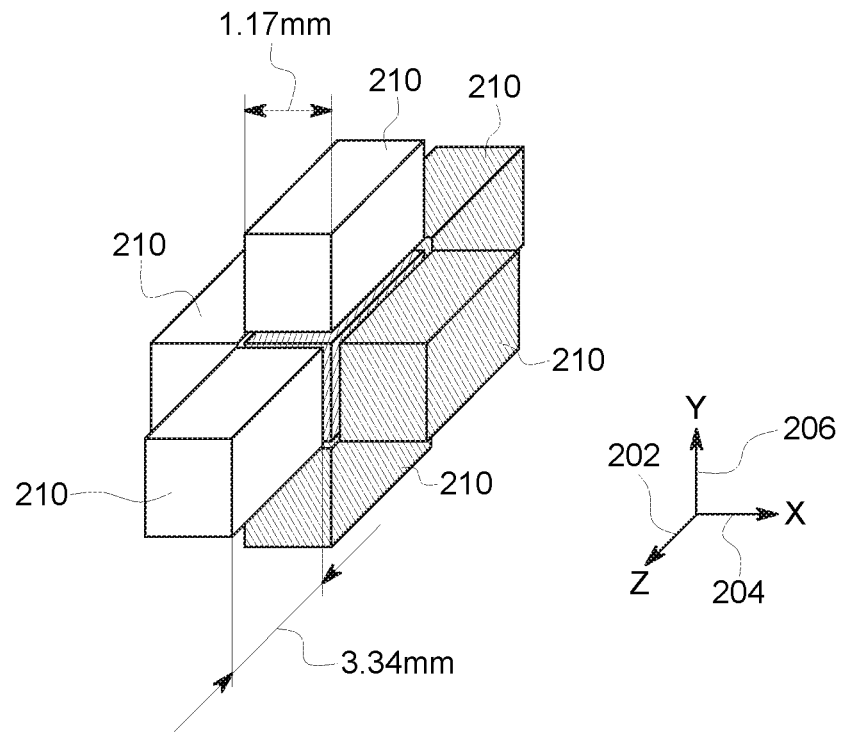
FIG. 2a provides a schematic view of voxels in accordance with various embodiments.
Figure 2B:
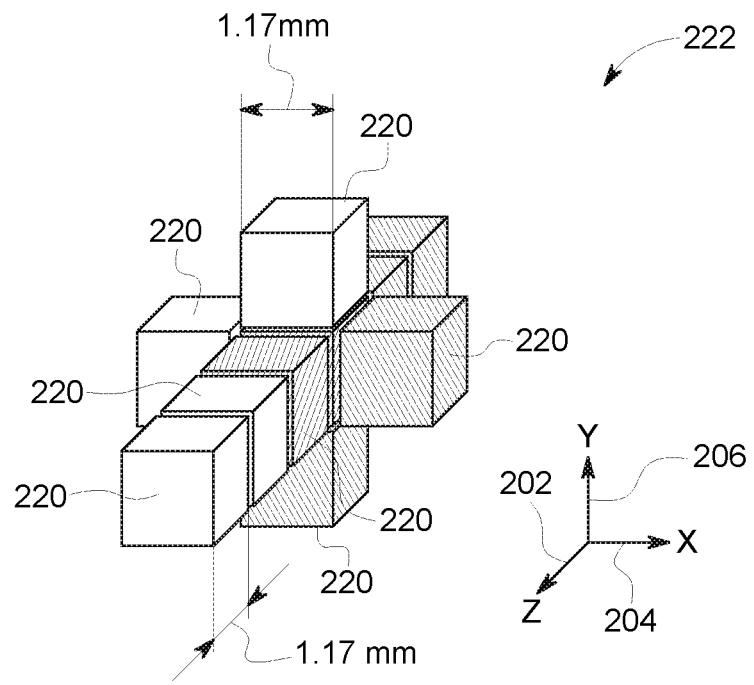
FIG. 2b provides a schematic view of voxels in accordance with various embodiments.

FIGS. 2a and 2b depict example concepts relating to interpolation of voxel sizes. For example, FIG. 2a depicts non-interpolated anisotropic voxels 210, and FIG. 2b depicts interpolated voxels 220. As seen in FIG. 2a, the voxels 210 have a greater magnitude along the axial direction 202 than along the transaxial directions 204, 206. For example, the voxels 210 may measure 3.34 millimeters along the axial direction 202 and 1.17 millimeters along the transaxial directions 204, 206. It may be noted that, while the given dimensions in the example are exactly twice as long along the axial direction 202 than along the transaxial directions 204, 206 for clarity of illustration, other dimensions and/or ratios between axial and transaxial dimensions may be utilized in other embodiments. In FIG. 2b, a linear interpolation has been applied to provide interpolated voxels 220. In the illustrated embodiment, the interpolated voxels are 1.17 millimeters in each dimension, and, accordingly, are isotropic. It may be noted that, in other embodiments, other types of interpolation (e.g., spline interpolation) may be applied. It may be further noted that, in various embodiments, the interpolated voxels 220 may not be precisely or exactly isotropic, but will more nearly approximate being isotropic than the non-interpolated anisotropic voxels 210.

Generally speaking, in various embodiments, an interpolation (e.g., linear interpolation) is applied to uneven voxel sizes (e.g., as seen in FIG. 2a) to make voxel size in an axial direction equal to or approximately equal to voxel size in transaxial directions (e.g., as seen in FIG. 2b). The interpolation may also be carried out in a transaxial direction to make isotropic voxels. The new interpolated matrix size is then used for penalty modulation (e.g., multiplication by $\sqrt{\beta_j \beta_k}$), with the matrix reverted back to original size (e.g., as seen in FIG. 2a) after the modulation operation. Accordingly, anisotropic smoothing involved in penalty generation is reduced or eliminated. It may be noted that, alternatively, the weights may be based on distance in physical length. For example, $w_{jk}=1/\text{sqrt}(sx^2+sy^2+sz^2)$ may be used where sx and sy are transaxial voxels sizes in the x and y directions, respectively, and sz is an axial voxel size in the z direction.

Accordingly, various embodiments address the challenge of increased smoothing in an axial direction and/or step artifacts resulting from anisotropic voxel in PL reconstruction algorithms for example in targeted reconstruction.

A technical effect provided by various embodiments includes reduction in over-smoothing along a direction (e.g., axial) and/or step artifacts. For example, over-smoothing and artifacts for images corresponding to coronal and/or sagittal planes for targeted reconstruction techniques are reduced in various embodiments. A technical effect of various embodiments includes increased contrast recovery from small lesions. A technical effect of various embodiments includes better quantitation and/or improved image quality. A technical effect of various embodiments included reduced statistical noise.

FIG. 1 provides a schematic block view of an imaging system 100 in accordance with various embodiments. The depicted imaging system 100 is configured to image an object 102 (e.g., a human patient or portion thereof). The imaging system 100 of the illustrated embodiment includes at least one detector 110, a processing unit 120, and a display unit 130. Generally, the detector 110 is used to detect imaging information corresponding to the object 120. The processing unit 120 receives the imaging information from the detector 110, and uses the imaging information to reconstruct an image corresponding to the object 102 or a portion thereof. The display unit 130 is used to display the image that has been reconstructed by the processing unit 120.

Generally speaking, the detector 110 is configured to acquire or detect imaging information regarding the object 102 that may be provided to the processing unit 120 and used to reconstruct an image. In various embodiments, the detector 110 may detect emissions of radioactivity from the object 102, such as emissions resulting from administration of a radiopharmaceutical to a human patient. For example, the detector 110 may be a PET detector. In the illustrated embodiment, the detector 110 is configured as a PET detector ring.

The depicted processing unit 120 is operably coupled to the detector 110, and is configured to (e.g., programmed to) acquire the imaging information from the detector 110 that has been acquired by the detector 110. Also, the processing unit 120 is configured to reconstruct an image (e.g., an image representing the object 102 or a portion thereof such as the brain or aspects of the brain). It may be noted that the image reconstructed by the processing unit 120 is organized into voxels having non-uniform dimensions (e.g., corresponding to the depiction of FIG. 2a). Voxels having non-uniform dimensions may also be referred to as anisotropic voxels.

The depicted processing unit 120 is configured to reconstruct the image by performing a PL image reconstruction using the imaging information. The PL image reconstruction includes performing a penalty function. It may be noted that the PL image reconstruction may be performed iteratively. In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, ASIC's, FPGA's, and/or computers, which may be integrated in a common housing or unit, or which may distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the acquisition of signals or imaging information, the interpolation of voxel sizes, the determination of penalty functions, and the maximization of objective functions for image reconstruction may rely on or utilize computations that may not be completed by a person within a reasonable time period. In the illustrated embodiment, the processing unit 120 includes a tangible, non-transitory memory 122 for storage of, among other things, instructions for causing the processing unit 120 to perform one or more steps or tasks discussed herein.

In various embodiments, the PL image reconstruction may include a number of steps. For example, an interpolation in one or more directions may be performed to address the anisotropic nature of the voxels of the acquired imaging direction. For example, a beta-map and emission image may be interpolated along an axial direction to provide interpolated voxels 220 from non-interpolated anisotropic voxels 210 as seen in FIGS. 2a and 2b, where the betamap comprises $\beta_j$'s. The interpolated voxels 220 may be isotropic, or, in various embodiments, may be approximately isotropic, or more isotropic than the non-interpolated voxels 210. The interpolation results in voxel sizes that are equal or approximately equal in all directions. For example, the voxel size for the voxel 220 in the axial direction 202 (or z direction) may be the same or approximately the same as the voxel size for the voxel 220 in the transaxial directions 204, 206 (or x and y directions, respectively).

Figure 2C:
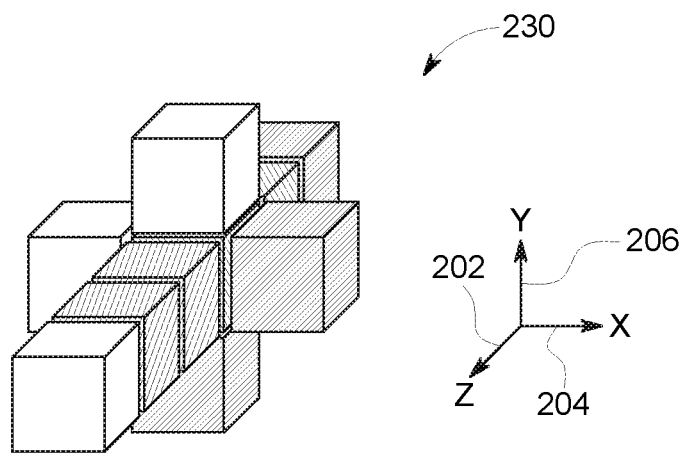
FIG. 2c provides a schematic view of voxels in accordance with various embodiments.

Next, a shift may be performed on the interpolated betamap and emission image, resulting in the interpolated image 222 being changed to the shifted image 230 shown in FIG. 2c, with the change in voxel shades corresponding to shifts. The penalty may be defined as a function of modulation (comprising $\beta_j$'s) and image difference, or Penalty=f (Modulation, DiffImage) where f calculates the gradient $\nabla R(x)$ of the penalty function and/or the penalty function value $R(x)$. In various embodiments, the Modulation may be defined as Modulation=sqrt(betamap*ShiftedBetamap), and DiffImage may be defined as DiffImage=(EmissionImage−ShiftedEmissionImage). The modulation and shifting are uniform in all directions due to the uniform voxel size provided by the interpolation.

The penalty thus determined using interpolated voxel size may be referred to as an interpolated penalty or an initial penalty, as it is determined using interpolated voxels, and is determined before other penalties. Next, the interpolated penalty (or initial penalty), may be interpolated back to the original size, to provide a modified penalty (which may also be referred to as an original size penalty). The original size penalty may then be used during the reconstruction process. For example, the modified penalty may be used in connection with block sequential regularized expectation maximization (BSREM) reconstruction process in various embodiments. Accordingly, in various embodiments, the processing unit 120 is configured to interpolate the voxel size only for determining the penalty function, and to not interpolate the voxel size for a remainder of the PL image reconstruction. Thus, the interpolated size may be used for determining the penalty function, while the original or non-interpolated size is used for the remainder of the PL image reconstruction.

In various embodiments, the processing unit 120 may be understood as performing a series of steps as part of performing the PL image reconstruction (and associated penalty function). For example, the processing unit 120 in various embodiments first interpolates a voxel size in at least one dimension (e.g., dimension 202) from an original size (e.g., as represented in FIG. 2*a*) to an interpolated size (e.g., as represented in FIG. 2*b*) before determining a penalty function. Next, the processing unit 120 determines the penalty function using the interpolated size to provide an initial penalty. Next, the processing unit 120 interpolates the initial penalty (or the penalty determined using the interpolated, uniform or approximately uniform voxel size) to the original size to provide a modified penalty. After determining the modified penalty, or the penalty corresponding to the original voxel size (the non-uniform or anisotropic voxel size), the modified penalty is applied in the PL image reconstruction or used in maximizing the PL objective function.

It may be noted that, in various embodiments, the processing unit 120 is configured to interpolate the voxel size in an axial direction, or along an axial direction. For example, the voxel may have a uniform size in transaxial directions (x and y directions, or 204 and 206 in FIGS. 2*a*-2*c*), but a size along an axial direction (z direction, or 202 in FIGS. 2*a*-2*c*) that differs from the size in the transaxial directions. The transaxial directions in various embodiments correspond to a length and width of the object 102 being imaged, and the axial direction corresponds to a depth or thickness of the object 102 being imaged. In various embodiments, the size of the voxel along the axial direction may be understood as corresponding to a slice thickness of acquired imaging information. Accordingly, an interpolation that interpolates an axial measure of a voxel to a size that is smaller than the original size may be understood as providing more slices of imaging data, or reducing an effective slice thickness of the imaging data.

In various embodiments, the processing unit 120 is configured to linearly interpolate the voxel size in at least one direction (e.g., along direction 202). As discussed herein, the interpolation may be performed to make the voxel size in the direction for which it is interpolated to be equal to the voxel sizes in other directions. It may be noted that the interpolation may be performed to make voxel sizes along one direction approximately equal to those in other directions, or to make the voxel size along one direction more closely match the size in other directions. The interpolated size accordingly is closer in size to the voxel sizes in other directions than the original, non-interpolated size. In some embodiments, the voxel size in a first direction may be understood to be approximately the same size as the voxel size in a second direction when the size in the first direction is within 10% or less of the voxel size in the second direction. It may further be noted that the size of the interpolated voxels along a given direction (e.g., direction 202) may not all have the same size along the given direction. For example, some voxels may have an interpolated size that is equal to the size along other directions, while other voxels may have an interpolated size that is approximately equal to the size along other directions. Other interpolation methods than linear interpolation may be used alternatively or additionally. For example, a spline interpolation may be performed in various embodiments.

Figure 3:
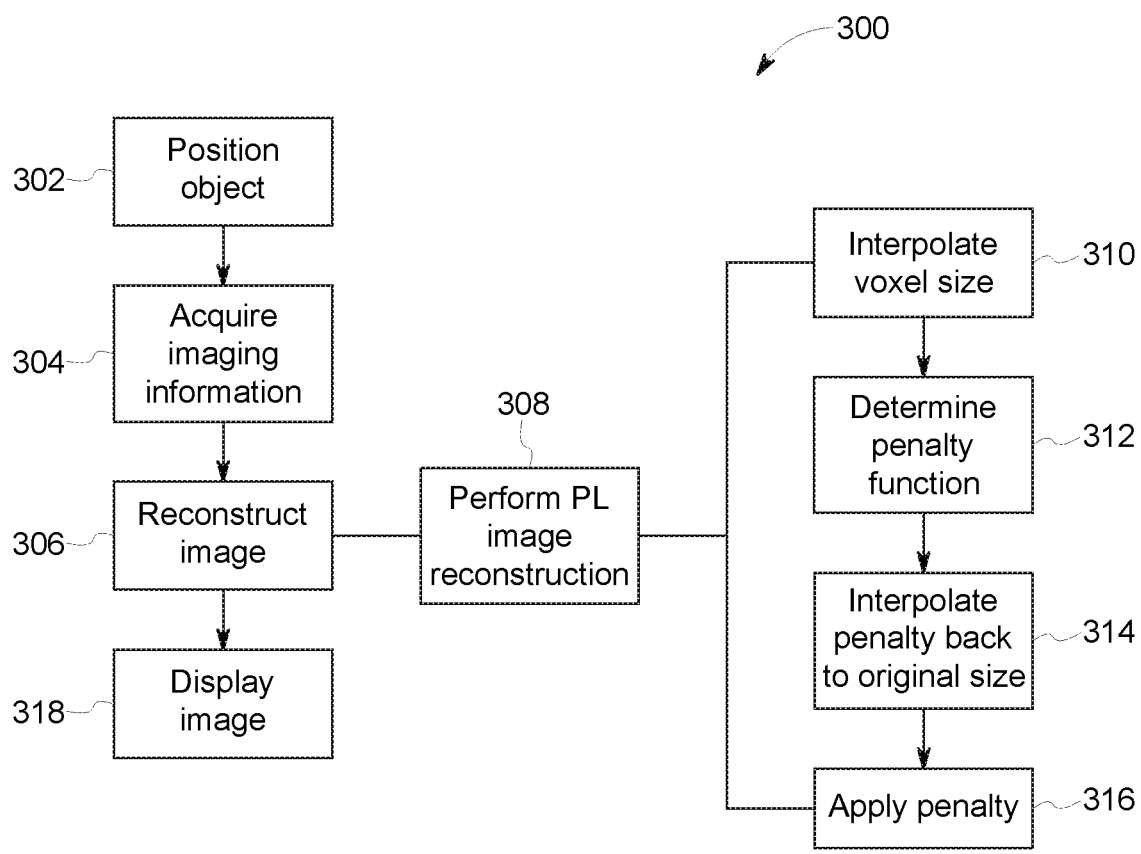
FIG. 3 illustrates a flowchart in accordance with various embodiments.

FIG. 3 illustrates a flowchart of a method 300. The operations of FIG. 3 may be implemented by one or more processors (e.g., processing unit 120) executing program instructions stored in memory (e.g., memory 122). The method 300, for example, may employ structures or aspects of various embodiments (e.g., systems and/or methods) discussed herein, such as the system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms to direct hardware (e.g., processing unit 120) to perform one or more operations described herein. It should be noted, other methods may be used, in accordance with embodiments herein.

At 302, an object to be imaged is positioned to be imaged by an imaging system (e.g., imaging system 100). For example, the object may be positioned within a field of view of one or more detectors of the system. The object to be imaged in various embodiments is a human patient or a portion thereof, such as the brain. In various embodiments, the patient to be imaged is administered a radiopharmaceutical, and the imaging is performed using detected emissions from the patient. For example, the imaging system 100 may be configured to perform PET imaging. Other modalities of imaging may be used additionally or alternatively to PET in various embodiments.

At 304, imaging information is acquired with at least one detector (e.g., detector 110). For example, as discussed herein, PET imaging information (e.g., sinogram data or list mode data) may be acquired. In various embodiments, the detector (or detectors) are operably coupled with at least one processor (e.g., processing unit 120), which receives the imaging information from the detector (or detectors) and reconstructs an image using the imaging information. The image is organized into voxels having non-uniform dimensions. Put another way, the voxel size in at least one direction is different than the voxel size in at least one other direction. For example, the voxel size in an axial direction (or z direction) may be different than the voxel size in a transaxial direction (or x and y directions).

At 306, an image is reconstructed (e.g., by processing unit 120) using the imaging information. In the illustrated embodiment, at 308, the image is reconstructed by performing a PL image reconstruction. The PL image reconstruction includes a penalty function as discussed herein. The PL image reconstruction, including determining or performing the penalty function, may be performed in a number of steps. Here determining or performing the penalty function may refer to calculating the gradient of the penalty function or the penalty function value. Accordingly, as used herein, determining or performing a penalty function may include calculating the gradient of the penalty function or the penalty function value unless expressly excluded.

For example, in the illustrated embodiment, at 310, a voxel size is interpolated in at least one dimension from an original size to an interpolated size before the penalty function (or the gradient of the penalty function) is determined. For example, where the size of the voxel in the axial direction is larger than the voxel size in the transaxial directions, the voxel sizes in the axial direction may be interpolated to have a size that is equal to or approximates the voxel size in the transaxial direction. The voxel size in various embodiments is interpolated linearly. Other interpolation techniques may be employed alternatively or additionally. It may be noted that the voxel size may be interpolated for determining the penalty function but not interpolated for a remainder of the PL image reconstruction. Accordingly, an interpolated voxel size may be used for determining the penalty function, but an original voxel size used for other aspects of the reconstruction.

At 312, the penalty function (or the gradient of the penalty function) is determined using the interpolated size. The determination of the penalty function (or the gradient of the penalty function) at 312 provides an initial penalty (or an initial penalty gradient), or a penalty (or a penalty gradient) using isotropic (or approximately isotropic) voxel sizes. At 314, the initial penalty (or the initial penalty gradient) is interpolated back to the original voxel size, or the voxel size before the interpolation performed at 310. Accordingly, a modified penalty (or a modified penalty gradient) is provided. Then, at 316, the modified penalty (or the modified penalty gradient) (or the penalty or the penalty gradient resulting from interpolation back to the original voxel size) is applied in the PL image reconstruction.

At 318, the image that has been generated or reconstructed using the PL image reconstruction is displayed (e.g., via display unit 130). The display, for example, may be provided as part of a visual display on a screen, as a printout or other tangible representation of the image, or via transmission of the image to a remote location.

Figure 4:
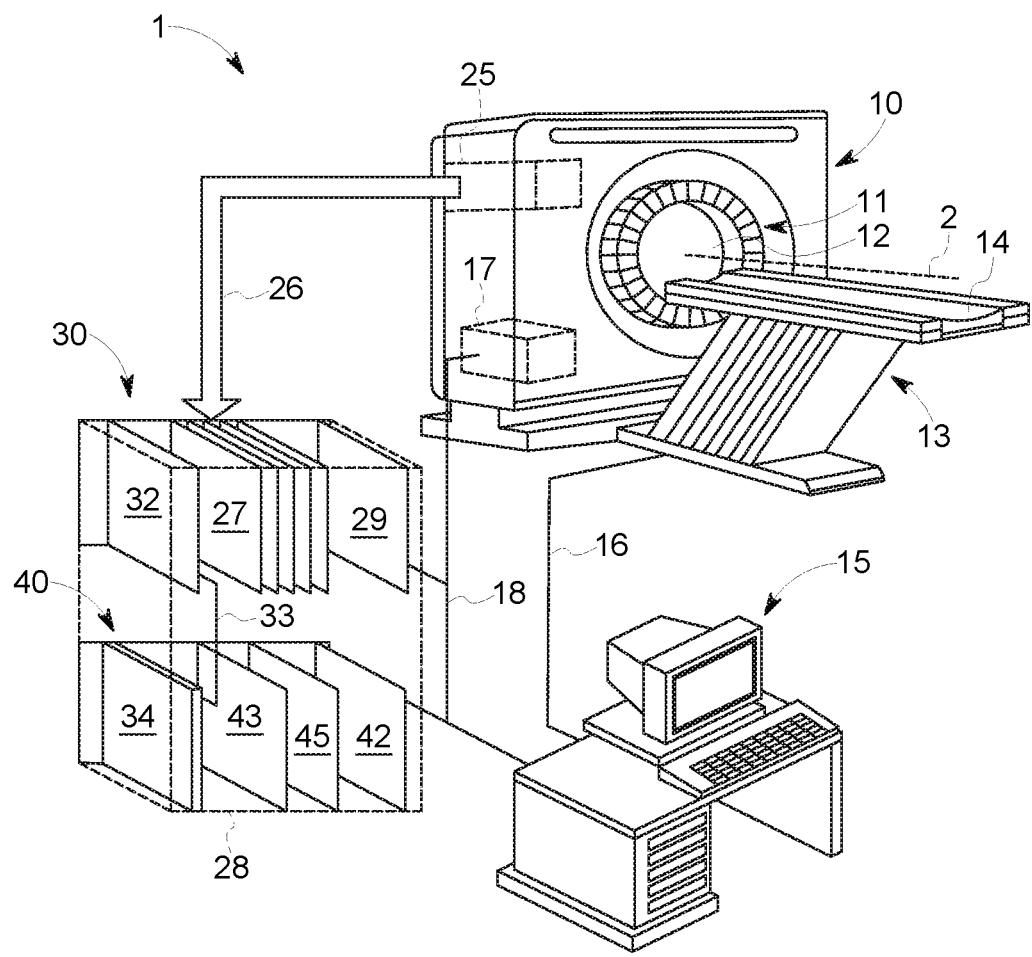
FIG. 4 illustrates an imaging system in accordance with various embodiments.
Figure 5:
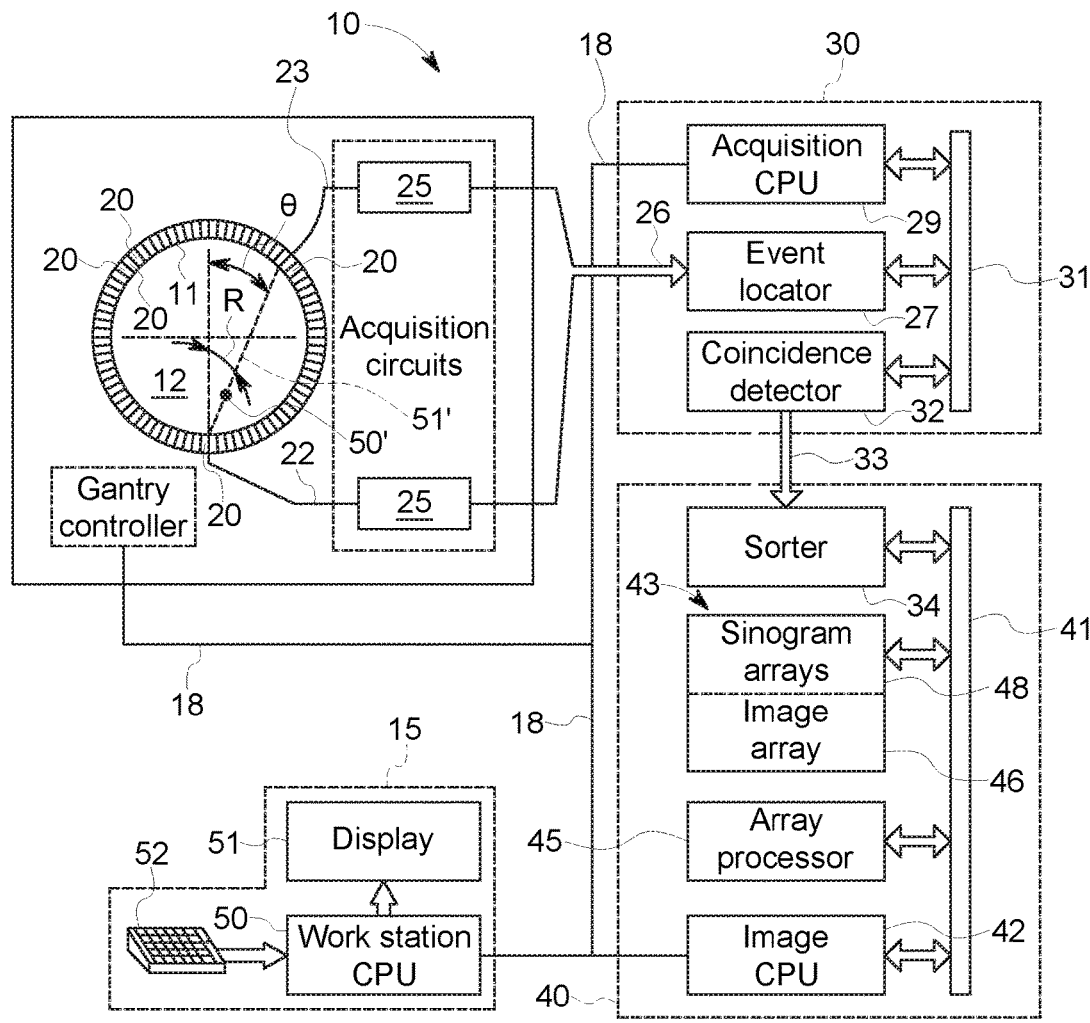
FIG. 5 is a schematic diagram of the imaging system of FIG. 4.
Figure 6:
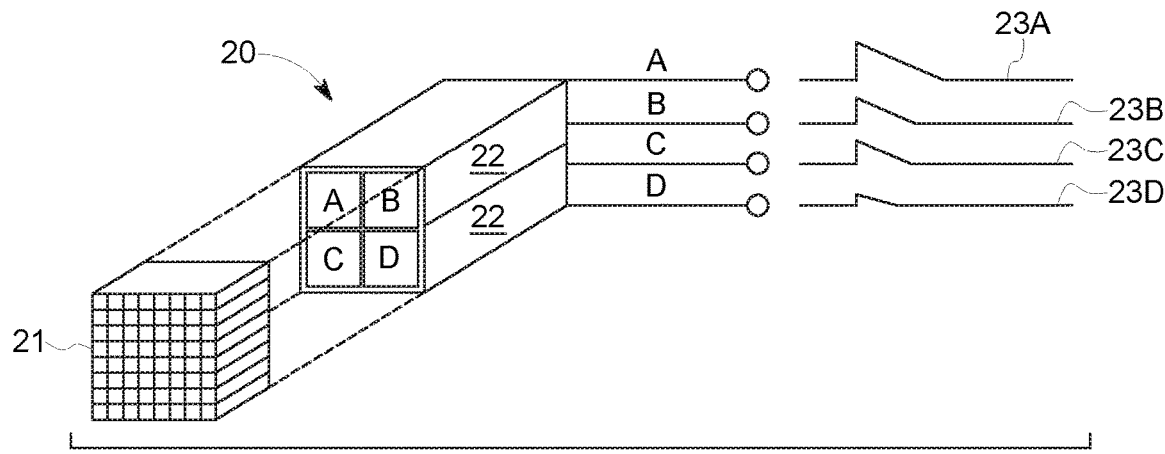
FIG. 6 illustrates an example of a detector module which forms part of the imaging system in accordance with various embodiments.

FIGS. 4-6 illustrate a PET imaging system with which various embodiments described herein may be employed. In other embodiments, crystal arrays as discussed herein may be utilized with other imaging systems (e.g., imaging systems configured for one or more additional or alternative modalities). FIG. 4 illustrates a PET scanning system 1 including a gantry 10 that supports a detector ring assembly 11 about a central opening or bore 12. The detector ring assembly 11 in the illustrated embodiments is generally circular and is made up of plural rings of detectors spaced along a central axis 2 to form a cylindrical detector ring assembly. In various embodiments, the detector ring assembly 11 may include 5 rings of detectors spaced along the central axis 2. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a communications link 16. A gantry controller 17 is mounted within the gantry 10 and is responsive to commands received from the operator work station 15 through a second communication link 18 to operate the gantry.

As shown in FIG. 5, the operator work station 15 includes a central processing unit (CPU) 50, a display 51, and a keyboard 52. An operator may use the keyboard to control the calibration of the PET scanner, the configuration of the PET scanner, and the positioning of the patient table for a scan. Also, the operator may control the display of the resulting image on the display 51 and/or perform image enhancement functions using programs executed by the work station CPU 50.

The detector ring assembly 11 includes a number of detector modules. For example, the detector ring assembly 11 may include 36 detector modules, with each detector module including eight detector blocks. An example of one detector block 20 is shown in FIG. 6. The detector blocks 20 in a detector module may be arranged, for example, in a 2×4 configuration such that the circumference of the detector ring assembly 11 is 72 blocks around, and the width of the detector assembly 11 is 4 detector blocks wide. Each detector block 20 may include a number of individual detector crystals. In the illustrated embodiment, the array of detector crystals 21 is situated in front of four photosensors 22. The photosensors 22 are depicted schematically as photomultiplier tubes; however, it may be noted that SiPM's may be employed in various embodiments. Other configurations, sized and numbers of detector crystals, photosensors and detector modules may be employed in various embodiments.

During a PET scan, an annihilation photon may impact one of the detector crystals 21. The detector crystal 21, which may be formed, for example of lutetium yttrium silicate (LYSO) or bismuth germinate (BGO), for example, converts the annihilation photon into a number of photons which are received and detected by the photosensors. The photons generated by a detector crystal generally spread out to a certain extent and travel into adjacent detector crystals such that each of the four photosensors 22 receives a certain number photons as a result of an annihilation photon impacting a single detector crystal 21.

In response to a scintillation event, each photosensor 22 produces a signal 23A-23D on one of the lines A-D, as shown in FIG. 6, which rises sharply when a scintillation event occurs and then tails off exponentially. The relative magnitudes of the signals are determined by the position in the detector crystal array at which the scintillation event took place. The energy of the annihilation photon which caused the scintillation event determines the total magnitude of the four signals. The time that the signal begins to rise is determined by when the scintillation event occurs and the time required for photons to travel from the position of the scintillation event to the photosensors. The example depicted in FIG. 6 provides an example based on a vacuum photodetector; however, it may be noted that certain principles disclosed herein may also be applied to SiPM detectors generally.

As shown in FIG. 5, a set of acquisition circuits 25 is mounted within the gantry 10 to receive the four signals from the detector block 20. The acquisition circuits 25 determine timing, energy and the event coordinates within the array of detector crystals using the relative signal strengths. The results are digitized and sent through a cable 26 to an event locator circuit 27 housed in a separate cabinet 28. Each acquisition circuit 25 also produces an event detection pulse which indicates the exact moment the scintillation event took place.

The event locator circuits 27 form part of a data acquisition processor 30 which periodically samples the signals produced by the acquisition circuits 25. The data acquisition processor 30 has an acquisition CPU 29 which controls communications on the local area network 18 and a bus 31. The event locator circuits 27 assemble the information regarding each valid event into a set of digital numbers that indicated when the event took place and the identity of the detector crystal 21 which detected the event. The event locator circuits 27, for example, may use a detector position map to map a pair of coordinates to the detector 21 which detected the event.

The event data packets are transmitted to a coincidence detector 32 which is also part of the data acquisition processor 30. The coincidence detector 32 accepts the event data packets from the event locator circuits 27 and determines if any two of them are in coincidence. Coincidence is determined by a number of factors. For example, time markers in each event data packet may be required to be within a specified time period of each other, e.g., 6 nanoseconds. As another example, the locations indicated by the two event data packets may be required to lie on a straight line which passes through the field of view (FOV) in the scanner bore 12. Events which cannot be paired are discarded, but coincident event pairs are located and recorded as a coincidence data packet that is transmitted through a serial link 33 to a sorter 34. The format of the coincidence data packet may be, for example, a thirty-two bit data stream which includes, among other things, a pair of digital numbers that precisely identify the locations of the two detector crystals 21 that detected the event.

The sorter 34, which may include a CPU and which forms part of an image reconstruction processor 40, receives the coincidence data packets from the coincidence detector 32. The function of the sorter 34 is to receive the coincidence data packets and allocate sinogram memory for the storage of the coincidence data. The set of all projection rays that point in the same direction ($\theta$) and pass through the scanner's field of view is a complete projection, or "view", which makes a set of sinogram. The distance (R) between a particular projection ray and the center of the field of view locates that projection ray within the view. As shown in FIG. 5, for example, an event 50' occurs along a projection ray 51' which is located in a view at the projection angle $\theta$ and the distance R. The sorter 34 counts all of the events that occur on this projection ray (R, $\theta$) during the scan by sorting out the coincidence data packets that indicate an event at the detector crystals 21 lying on the projection ray. During an emission scan, the coincidence counts are organized in memory 43, for example as a set of two-dimensional array, one for each axial image, and each having as one of its dimensions the projection angle $\theta$ and the other dimension the distance R. This $\theta$ by R map of the measured events may be referred to as sinogram array 48. The sorter 34 may also organize the coincidence events into other data formats. In a projection plane format, for example, other variables may be used to define coincidence events which are detected by pairs of detector crystals 21 in non-adjacent detector rings.

Coincidence events occur at random and the sorter 34 determines the $\theta$ and R values from the two crystal addresses in each coincidence data packet and increments the count of the corresponding sinogram array element. At the completion of the emission scan, the sinogram array 48 stores the total number of annihilation events which occurred along each ray. The array processor 45 reconstructs an image from the data in the sinogram array 48. First, however, a number of corrections may be made to the acquired data to correct for measurement errors such as those caused by attenuation of annihilation photons by the patient, detector gain non-uniformities, random coincidences, and integrator dead time. Each row of the corrected sinogram array is then Fourier transformed by the array processor 45 and multiplied by a one-dimensional filter array. The filtered data is then inverse Fourier transformed, and each array element is back projected to form the image array 46. The image CPU 42 may either store the image array data or output the data to the operator work station 15. Alternatively, the image array 46 may be generated by an iterative image reconstruction algorithm run by the array processor 45 and/or the image CPU 42.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation).

For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A system comprising:
   at least one detector configured to acquire imaging information;
   a microprocessor operably coupled to the at least one detector and configured to acquire the imaging information from the at least one detector, the microprocessor configured to reconstruct an image using the imaging information, wherein the imaging information is organized into voxels having non-uniform dimensions, the microprocessor configured to:
   perform a penalized likelihood (PL) image reconstruction using the imaging information, the PL image reconstruction comprising a penalty function, wherein performing the penalty function comprises:
      interpolating a voxel size in at least one dimension from an original size to an interpolated size before determining a penalty function;
      determining the penalty function using the interpolated size to provide an initial penalty;
      interpolating the initial penalty to the original size to provide a modified penalty; and
      applying the modified penalty in the PL image reconstruction; and
   a display unit configured to display the image generated using the PL image reconstruction.

2. The system of claim 1, wherein processing unit is configured to interpolate the voxel size in an axial direction.

3. The system of claim 1, wherein the processing unit is configured to linearly interpolate the voxel size in the at least one direction.

4. The system of claim 1, wherein the processing unit is configured to interpolate the voxel size only for determining the penalty function, and to not interpolate the voxel size for a remainder of the PL image reconstruction.

5. The system of claim 1, wherein the penalty function is expressed as:

$$\Phi(x) = \Sigma_i y_i \log([Px]_i + r_i) - ([Px]_i + r_i) - \beta R(x),$$

where x denotes a vector representing the image, $y_i$ are emission sinogram data, P represents a forward projection operator which includes attenuation, normalization and point spread function resolution modeling, $r_i$ are estimated back round contributions including scatter and randoms, R(x) is a penalty function and $\beta$ is a penalty parameter.

6. The system of claim 1, wherein the processing unit is configured to maximize the following objective function to perform the PL image reconstruction:

$$R(x) = \Sigma_j \Sigma_{k \in N_j} w_{jk} \sqrt{\beta_j \beta_k} \frac{(x_j - x_k)^2}{x_j + x_k + \gamma |x_j - x_k|},$$

where x denotes a vector representing the image, $N_j$ is a set of voxels neighboring voxel j, $w_{jk}$ are weights, $\beta_j$, $\beta_k$ are penalty modulation factors and $\gamma$ is a parameter that controls the degree of edge-preservation.

7. The system of claim 1, wherein the at least one detector comprises at least one positron emission tomography (PET) detector.

8. A method comprising:
   acquiring, with at least one detector, imaging information;
   reconstructing an image using the imaging information, wherein the imaging information is organized into voxels having non-uniform dimensions, wherein reconstructing the image comprises:
   performing a penalized likelihood (PL) image reconstruction using the imaging information, the PL image reconstruction comprising a penalty function, wherein performing the penalty function comprises:
      interpolating a voxel size in at least one dimension from an original size to an interpolated size before determining a penalty function;
      determining the penalty function using the interpolated size to provide an initial penalty;
      interpolating the initial penalty to the original size to provide a modified penalty; and
      applying the modified penalty in the PL image reconstruction; and displaying the image generated using the PL image reconstruction.

9. The method of claim 8, further comprising interpolating the voxel size in an axial direction.

10. The method of claim 8, further comprising linearly interpolating the voxel size in the at least one direction.

11. The method of claim 8, further comprising interpolating the voxel size only for determining the penalty function, and to not interpolating the voxel size for a remainder of the PL image reconstruction.

12. The method of claim 8, wherein the penalty function is expressed as:

$$\Phi(x)=\Sigma_i y_i \log([Px]_i+r_i)-([Px]_i+r_i)-\beta R(x),$$

where x denotes a vector representing the image, $y_i$ are emission sinogram data, P represents a forward projection operator which includes attenuation, normalization and point spread function resolution modeling, $r_i$ are estimated background contributions including scatter and randoms, R(x) is a penalty function and β is a penalty parameter.

13. The method of claim 8, wherein the processing unit is configured to maximize the following objective function to perform the PL image reconstruction:

$$R(x) = \Sigma_j \Sigma_{k \in N_j} w_{jk} \sqrt{\beta_j \beta_k} \frac{(x_j - x_k)^2}{x_j + x_k + \gamma|x_j - x_k|},$$

where x denotes a vector representing the image, $N_j$ is a set of voxels neighboring voxel j, $w_{jk}$ are weights, $\beta_j$, $\beta_k$ are penalty modulation factors and γ is a parameter that controls the degree of edge-preservation.

14. The method of claim 8, wherein acquiring the imaging information comprises acquiring positron emission tomography (PET) imaging information with a PET detector.

15. A tangible and non-transitory computer-readable medium having instructions stored thereon, the instructions, when executed by a computer, causing the computer to:
acquire, with at least one detector, imaging information;
reconstruct an image using the imaging information, wherein the imaging information is organized into voxels having non-uniform dimensions, wherein reconstructing the image comprises:
performing a penalized likelihood (PL) image reconstruction using the imaging information, the PL image reconstruction comprising a penalty function, wherein performing the penalty function comprises:
interpolating a voxel size in at least one dimension from an original size to an interpolated size before determining a penalty function;
determining the penalty function using the interpolated size to provide an initial penalty;
interpolating the initial penalty to the original size to provide a modified penalty; and
applying the modified penalty in the PL image reconstruction; and
display the image generated using the PL image reconstruction.

16. The computer-readable medium of claim 15, wherein performing the PL image reconstruction further comprises interpolating the voxel size in an axial direction.

17. The computer-readable medium of claim 15, wherein performing the PL image reconstruction further comprises linearly interpolating the voxel size in the at least one direction.

18. The computer-readable medium of claim 15, wherein performing the PL image reconstruction further comprises interpolating the voxel size only for determining the penalty function, and to not interpolating the voxel size for a remainder of the PL image reconstruction.

19. The computer-readable medium of claim 15, wherein the penalty function is expressed as:

$$\Phi(x)=\Sigma_i y_i \log([Px]_i+r_i)-([Px]_i+r_i)-\beta R(x),$$

where x denotes a vector representing the image, $y_i$ are emission sinogram data, P represents a forward projection operator which includes attenuation, normalization and point spread function resolution modeling, $r_i$ are estimated background contributions including scatter and randoms, R(x) is a penalty function and β is a penalty parameter.

20. The computer-readable medium of claim 15, wherein performing the PL image reconstruction further comprises maximizing the following objective function to perform the PL image reconstruction:

$$R(x) = \Sigma_j \Sigma_{k \in N_j} w_{jk} \sqrt{\beta_j \beta_k} \frac{(x_j - x_k)^2}{x_j + x_k + \gamma|x_j - x_k|},$$

where x denotes a vector representing the image, $N_j$ is a set of voxels neighboring voxel j, $w_{jk}$ are weights, $\beta_j$, $\beta_k$ are penalty modulation factors and γ is a parameter that controls the degree of edge-preservation.

* * * * *